(12) United States Patent
Noordhoek

(10) Patent No.: US 9,545,232 B2
(45) Date of Patent: Jan. 17, 2017

(54) METAL ARTEFACT PREVENTION DURING NEEDLE GUIDANCE UNDER (XPER) CT

(75) Inventor: Nicolaas Jan Noordhoek, Breda (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 928 days.

(21) Appl. No.: 12/514,337

(22) PCT Filed: Oct. 30, 2007

(86) PCT No.: PCT/IB2007/054396
§ 371 (c)(1),
(2), (4) Date: May 11, 2009

(87) PCT Pub. No.: WO2008/056298
PCT Pub. Date: May 15, 2008

(65) Prior Publication Data
US 2010/0290583 A1    Nov. 18, 2010

(30) Foreign Application Priority Data

Nov. 10, 2006 (EP) .................................. 06123818

(51) Int. Cl.
*A61B 6/00* (2006.01)
*A61B 6/12* (2006.01)

(52) U.S. Cl.
CPC ................ *A61B 6/12* (2013.01); *A61B 6/547* (2013.01); *A61B 6/4441* (2013.01); *A61B 34/20* (2016.02);
(Continued)

(58) Field of Classification Search
CPC ......... A61B 6/12; A61B 6/547; A61B 6/4441; A61B 2019/5251; A61B 2019/5238; A61B 19/5244
See application file for complete search history.

(56) References Cited

U.S. PATENT DOCUMENTS 5,632,275 A *  5/1997  Browne et al. ............... 600/425
5,736,930 A     4/1998  Cappels
(Continued)

FOREIGN PATENT DOCUMENTS

DE    102005012985 A1    7/2006
JP         10211197 A1    8/1998
(Continued)

OTHER PUBLICATIONS

Man et al., Metal Streak Artifacts in X-ray Computed Tomography: A Simulation Study, IEEE Transactions on Nuclear Science, vol. 46, No. 3, Jun. 1999.*
(Continued)

*Primary Examiner* — Bo J Peng

(57) ABSTRACT

The present invention relates to a method and device for preventing metal artifacts computer tomography scans made during biopsy taking, when a metal needle is present in the field of view of a scan. The direction of the metal needle and the direction of the electro-magnetic field are determined in advance. For the determination of the electro-magnetic field a position of a source of the electro-magnetic field a position of a detector are considered. The user may be warned, when the determined direction of the electro-magnetic field and of the direction of the metallic needle correspond to each other.

24 Claims, 4 Drawing Sheets

(52) U.S. Cl.
CPC .. *A61B 2034/2051* (2016.02); *A61B 2090/376* (2016.02)

(56) References Cited

U.S. PATENT DOCUMENTS

| | | | | |
|---|---|---|---|---|
| 5,769,086 A | * | 6/1998 | Ritchart et al. | 600/566 |
| 5,799,055 A | | 8/1998 | Peshkin et al. | |
| 6,092,928 A | * | 7/2000 | Mattson et al. | 378/205 |
| 6,198,790 B1 | * | 3/2001 | Pflaum | 378/9 |
| 6,341,152 B1 | * | 1/2002 | Sugihara | 378/4 |
| 6,423,009 B1 | * | 7/2002 | Downey et al. | 600/461 |
| 6,461,040 B1 | * | 10/2002 | Mattson et al. | 378/205 |
| 6,529,766 B1 | | 3/2003 | Guendel | |
| 6,817,762 B2 | * | 11/2004 | Proksa | 378/206 |
| 7,612,773 B2 | | 11/2009 | Magnin | |
| 8,600,141 B2 | | 12/2013 | Elter | |
| 8,837,681 B2 | | 9/2014 | Liu | |
| 8,995,735 B2 | | 3/2015 | Cao | |
| 2001/0012327 A1 | | 8/2001 | Loser | |
| 2004/0015070 A1 | * | 1/2004 | Liang et al. | 600/407 |
| 2004/0247070 A1 | | 12/2004 | Ali et al. | |
| 2006/0039591 A1 | * | 2/2006 | Zettel | A61B 6/032 382/132 |
| 2006/0120505 A1 | | 6/2006 | Seto et al. | |
| 2006/0182225 A1 | * | 8/2006 | Besson | 378/146 |

FOREIGN PATENT DOCUMENTS

| | | | |
|---|---|---|---|
| JP | 2000217811 A | * | 8/2000 |
| WO | WO 2005086062 A2 | * | 9/2005 |
| WO | 2007095330 A2 | | 8/2007 |

OTHER PUBLICATIONS

Xiao et al: "Software Design of Transperineal Prostate Needle Biopsy Robot": Proceedings of the 2005 IEEE Conference on Control Applications, Toronto, Canada, Aug. 28-31, 2005, pp. 13-18.

Liu, H.: "Metallic Needle Artifacts in Magnetic Resonance Imaging"; Journal of Applied Physics, Jun. 1, 1998, vol. 83, No. 11, pp. 6849-6851.

* cited by examiner

METAL ARTEFACT PREVENTION DURING NEEDLE GUIDANCE UNDER (XPER) CT

The present invention relates to a method and device for metal artefact prevention during needle guidance under (Xper) CT, and in particular to a method and device for preventing metal artefacts in (Xper) CT scans made during, for example, biopsy taking, when a metal needle is present in the field of view of an (Xper) CT scan.

BACKGROUND OF THE PRESENT INVENTION

Often repeated scans are made during biopsy, draining or vertebroplasty procedures. When a needle is positioned parallel to the X-ray path of an only single projection, serious metal artefacts will occur, which can completely obscure the lesion that is target of the biopsy, draining or vertebroplasty procedure.

Several applications exist, which are used to plan a needle track in a patient, based on a reconstructed volume of that patient. During biopsy taking, for example, several scans are made to verify the progress of the needle towards, for example, a tumour. These applications can make use of computer tomography scan volumes, and in particular of (Xper) CT scan volumes. An (Xper) CT scan consists of a rotational X-ray acquisition. When in one or more X-ray projections the needle is parallel to the path of the X-ray from, for example, an X-ray tube to a detector pixel, very strong metal artefacts occur that are nearly impossible to correct for and that will completely obscure the target lesion.

From JP10211197 A an X-ray CT device is known, wherein the scanning surface of a subject is irradiated with X-ray pulses from an X-ray source, a transmission X-ray amount is detected in an X-ray detector and the conversion output is amplified in a pre-amplifier part, A/D converted and inputted to an image processor. Then, after inputted X-ray transmission data for 360° are converted to the projection data and inverse projection data, the inverse projection data for 360° are added and the tomographic images are reconstituted and displayed at a monitor. At the time the measurement start angle is adjusted so as not to overlap the piercing angle of the piercing needle inserted to the testee body and the measurement start angle of the projected data and an angle 180° opposing the measurement start angle and artefacts generated by the movement during scanning of the piercing needle are suppressed.

Further H. Liu describes 'metallic needle artefacts in magnetic resonance imaging' in Journal of Applied Physics 83 (11), 1998, pages 6849-6851. D. Xiao et al, describe 'software design of transperineal prostate needle biopsy robot' in the proceeding of the IEEE conference control applications, Canada, 2005, pages 13-18.

SUMMARY OF THE INVENTION

It would be desirable to provide a method and device allowing to avoid metal artefacts during an imaging.

The invention provides a method for preventing metal artefacts during needle guidance, a corresponding device, an examination exposure device, a program element and a corresponding computer readable medium.

According to one aspect of the present invention a method is provided for metal artefact prevention during metallic needle guidance within an electromagnetic field of an examination exposure device, comprising determining a position of source of the electromagnetic field, determining a position of a detector, determining a direction of the electromagnetic field based on the position of the source and the position of the detector, determining a direction of the metal needle in the electromagnetic field, and providing a signal based on a comparison of the determined direction of the electromagnetic field and of the direction of the metallic needle. It is possible to use the geometrical calibration data used for the controlling of a gantry of an examination exposure apparatus. The method allows to indicate the paths that, for example, the biopsy needle should not follow to prevent metal artefacts. The information of the signal is used to warn the user for paths that are prone to result in metal artefacts and thus lead to useless (Xper) CT scans.

According to a further aspect of the present invention the electromagnetic field is an X-ray field, and the source is an X-ray focal spot and/or the detector is a detector pixel. Thus, the X-ray focal spot for each projection and the detector pixel position for each projection constitute the geometrical calibration data for determining the geometry of the source and the inventory of the environment influencing the determination of the x-ray field. Determination of the x-ray field includes determining the strength and the direction of the field, however is not limited thereto.

According to another aspect of the present invention the method further comprises determining field influencing parameters and determining the direction of the electromagnetic field based additionally on the field influencing parameters. Therefore, it is possible to consider, for example, environment parameters like inventory of the examination apparatus influencing the field distribution and to determine the direction of the electromagnetic field, which may be influenced by the environment, for example, metal or magnetic components.

According to a further aspect of the present invention, the method comprises providing a warning to the user. Warning a user during the needle track planning helps to prevent metal artefacts occurring when in one or more projections the needle will be parallel to the local X-ray beam. This is especially helpful for (Xper) CT, since (Xper) CT has a wide X-ray cone beam and it is far from trivial to the user when the path that he is planning will cause metal artefacts, that will both depend on the insertion point that is chosen and on the needle angle that is chosen.

According to a further aspect providing a warning to the user includes the provision of a vector map over a reconstructed volume that shows the paths of an X-ray cone beam through the reconstruction, which are the needle directions that should be prevented. With such an vector map the user does not only know that the present position probably leads to metal artefacts, but also knows which position have to be avoided in a further action.

According to a further aspect the method comprises providing an alternative position of an object to be examined to be treated with the needle such that the direction of the needle is not within paths of the X-ray cone beam through the reconstruction, which are the needle directions that should be prevented. Thus, the user can change the position of the object to be examined without the need to change the position of the needle with respect to the object to be examined.

According to another aspect, the method comprises an automatic positioning of the object to be examined such that the direction of the needle is not within paths of an X-ray cone beam through the reconstruction which are the needle directions that should be prevented. Thus, an erroneous decision and action of the user may be avoided. For sake of security, the use may be asked for acknowledgement or acceptance of the alternative position before the system automatically sets the new position. Any emergency interruption or monitoring for providing any serious collisions may be provided.

The method can warn the user in several ways, simply giving a warning when the planned needle track is in a so-called danger zone for metal artefacts, providing a vector map over the reconstructed volume, that shows the paths of the X-ray cone beam through the reconstruction, which are the needle directions that should be prevented, and/or when the planned path is critical and cannot easily be adapted (such as in the case of vertebroplasty), to advise to shift the patient. Further, it is an option to advise how much to shift the patient in form of, for example, a table movement, or to automatically shifting the patient. Since the entire geometry of the C-arm rotation is calibrated very accurately, it is possible to achieve very exact results. When providing the user with a warning, the user can modify the path planning. This can easily be achieved with a slight change of the angle of approach. It is also an option to shift the patient, when the planned path is critical and cannot easily be adapted, like vertebroplasty. In particular, the method can be used to plan the path of the needle, which can be augmented, to warn the user that the planned path lies in the plain of rotation, resulting in metal artefacts that render the scans useless.

According to another aspect, the examination exposure device is a computer tomography.

According to a further aspect, a device 10 is provided for metal artefact prevention during metallic needle guidance within an electromagnetic field 20 of an examination exposure device 1, comprising an element 11 adapted for determining a position of a source 21 of the electromagnetic field, an element 12 adapted for determining a position of a detector 25, an element 14 adapted for determining a direction 29 of the electromagnetic field based on the position of the source and the position of the detector, an element 16 for determining the direction 49 of the metallic needle 40, and an element 17 adapted for providing a signal based on a comparison of the determined direction 29 of the electromagnetic field and of the direction 49 of the metallic needle 40.

According to another aspect, the device comprises an element adapted for determining field influencing parameters and an element adapted for determining the direction of the electromagnetic field based additionally on the field influencing parameters. Thus, it is possible to consider components in the environment of the device influencing the magnetic field, for example (ferro-) magnetic elements and permanent magnets.

According to another aspect, the device comprises an element adapted for providing a warning to the user.

According to another aspect, the element for providing a warning to the user comprises an element adapted for providing a vector map over a reconstructed volume that shows the path of an X-ray cone beam through the reconstruction, which are the needle directions that should be prevented.

According to another aspect, the device comprises an element adapted for providing an alternative position of the object to be examined to be treated with the needle, such that the direction of the needle is not within paths of an X-ray cone beam through the reconstruction, which are the needle directions that should be prevented.

According to another aspect, the device comprises an element adapted for automatic positioning of the object to be examined such that the direction of the needle is not within paths of an X-ray cone beam through the reconstruction, which are the needle directions that should be prevented.

It should be noted that instead of an automatic positioning, the device may also be capable of only warning and/or advising the user for a new positioning or to ask for acceptance to proceed with an automatic positioning of the object to be examined.

According to another aspect, a computer tomography unit comprises the inventive device.

It should be noted that the electromagnetic field may be an X-ray field, however, the person skilled in the art may also adapt the inventive method and device for electromagnetic fields other than X-ray fields. According to a further aspect, the source may be an X-ray focal spot, and/or the detector may be a detector pixel.

According to another aspect, there is provided a programme element, which, when being executed by a processor, is adapted to carry out the inventive method.

According to another aspect, there is provided a computer readable medium having stored thereon the inventive programme element.

It should be noted that the subject matter of the present invention may be applied to any 3D X-ray application (3DRA, Xper CT, CT) that is used in combination with strongly absorbing elongated instruments that are scanned together with the patient. These may be, for example, biopsy taking, drainage, or vertebroplasty (screws). Xper CT is a system, which provides soft tissue imaging capabilities in the interventional suite without the need to transport the patient. Applications therefore include evaluation of soft tissue information before and immediately after the intervention, and detection of bleeding areas and calcifications. Xper CT reconstructions designed for interventional use take only a few minutes from acquisition to display, which is especially important in critical situations when the patient's condition may have deteriorated.

It may be seen as an gist of the present invention to avoid disturbances in imaging due to the position of a needle in advance by determining the position of the needle in advance and to predict possible metal artefacts.

These and other aspects of the present invention will become apparent from and elucidated with reference to the embodiments described hereinafter.

BRIEF DESCRIPTION OF THE FIGURES

Exemplary embodiments of the present invention will be described in the following with reference to the following drawings.

FIG. 1 describes the flow of the method according to one aspect of the present invention. It should be noted that the method components or steps do not have to be carried out in the description order, and that it is possible to change the sequence where it is appropriate.

Figure 1:
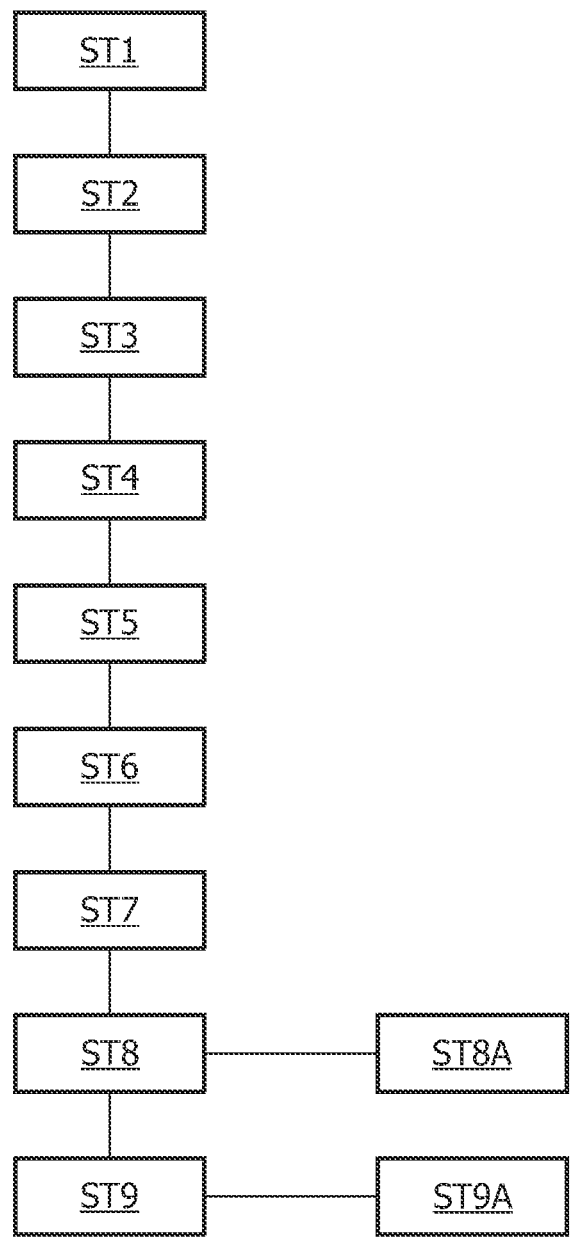
FIG. 1 is a diagram illustrating the method according to one aspect of the present invention.

With respect to FIG. 1, a method for metal artefact prevention during metallic needle guidance within an electromagnetic field of an examination exposure device comprises determining ST1 a position of a source of the electromagnetic field, determining ST2 a position of a detector, determining ST4 a direction of the electromagnetic field based on the position of the source and the position of the detector, determining ST6 a direction of the metal needle in the electromagnetic field, and providing ST7 a signal based on a comparison of the determined direction of the electromagnetic field and the direction of the metallic needle. It should be noted that in particular the sequence of the method components ST1 and ST2 may be changed where it is appropriate. Further the method component ST6 may be before or after the method components ST1, ST2 and ST4, respectively.

Figure 2:
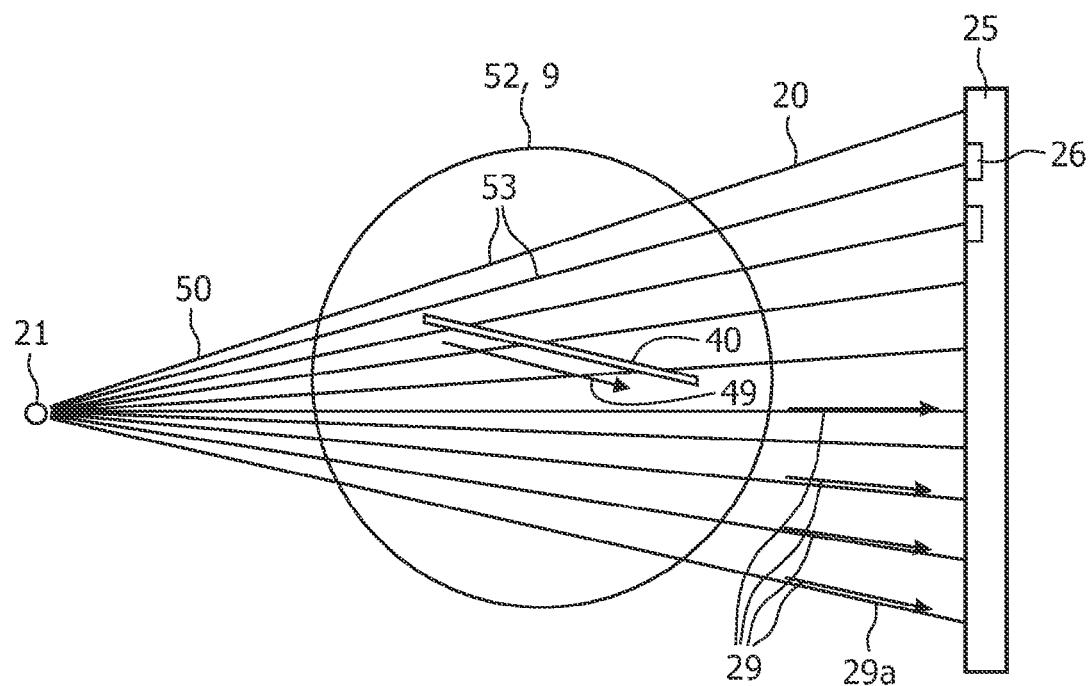
FIG. 2 illustrates the direction of the electromagnetic field and the direction of the needle.
Figure 4:
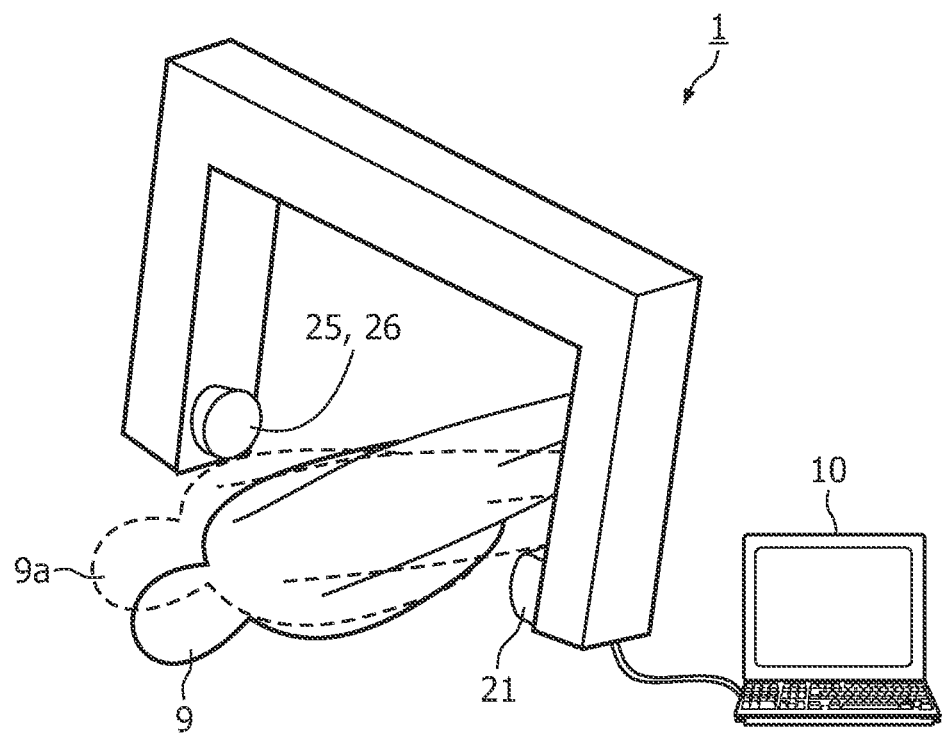
FIG. 4 illustrates an examination exposure device.

With respect further to FIG. 2 and FIG. 4, the determination of a position of a source 21 may be carried out based on control data used for controlling an examination exposure device, in particular to the control of the movement of the C-arm, since the entire geometry of the C-arm rotation is calibrated very accurately in available examination exposure devices. The determination of a position of a detector 25, 26 may be carried out in the same way. The determination of a direction 29 of the electromagnetic field 20 is carried out based on the position of the source 21 and the position of the detector 25, 26. The determination can be carried out in Cartesian coordinates, cylinder coordinates or spherical coordinates, however it is not limited thereto. The determination of a direction 49 of the metallic needle 40 in the electromagnetic field 20 can be carried out by detecting the metallic needle by the examination exposure device, in particular based on the picture processing of the results from the examination exposure device. If the direction 49 of the metallic needle 40 and the electromagnetic field 20 corresponds to the direction 29 of the electromagnetic field 20, a signal is provided. It should be noted that corresponding directions 49, 29 of the metallic needle 40 and the electromagnetic field 20 also include parallel vectors instead of congruent vectors. It should be also noted that it is possible to provide a signal in an inversed manner, in particular when the direction of the electromagnetic field and the direction of the metallic needle do not correspond, so that the signal then is an indication that the direction of the electromagnetic field and the direction of the metallic needle do not correspond.

With respect to FIG. 1, it is further possible to include a further method components of determining field influencing parameters ST3 and determining the direction 29 of the electromagnetic field 20 based on additionally the field influencing parameter ST5. These further steps are useful, if the environment includes components influencing the electromagnetic field so that the electromagnetic field is disturbed, and therefore has to be corrected considering the field influencing parameters. Field influencing parameters may occur due to housing components of the examination exposure device, however, are not limited thereto.

With respect to FIG. 1, it is further possible to include a further method component of providing a warning to the user based on the signal ST8. Thus, the signal may be used as a basis for providing the user with a warning or an advice that metal artefacts are likely and therefore, metal artefact during metallic needle guidance may be prevented. As a further method component the user may be provided ST8A with a vector map 51 over a reconstructed volume 52 that shows the paths 53 of an X-ray cone beam 50 through the reconstruction which are the needle directions that should be prevented. Thus, it is much easier for the user to estimate which needle directions lead to metal artefacts.

As a further method component an alternative position 9A of an object to be examined 9 may be provided ST9, so that the object to be examined 9 to be treated with a needle can be moved in an alternative position 9A such that the direction of the needle 49 is not within paths 53 of an X-ray cone beam 50 through the reconstruction, which are the needle directions 49 that should be prevented. Shifting the object to be examined allows to maintain the position of the needle relative to the position of the object to be examined.

Further, the method component of automatic positioning ST9A may be provided so that the user may only accept or confirm the suggestion of the system so that an automatic positioning can be carried out. Thus, any erroneous decision or action of the user may be avoided.

FIG. 2 shows the electromagnetic field without field influencing parameters, so that the electromagnetic field is only influenced by the source 21. The detector 25 may also influence the field. However it is useful to determine the electro-magnetic field in particular in the range of the streamlines of the field which cross the relevant detector 25, 26 detecting possibly the artefact. The detector may include detector pixels 26 the number of which depends on the resolution of the pictures to be achieved.

In FIG. 2 the object to be examined corresponds to the reconstructed volume 52, 9. The direction of the electromagnetic field 20 is indicated with arrows 29, 29A. A needle 40 is illustrated within the object to be examined 9, wherein the direction of the needle is indicated with an arrow 49. In the case of FIG. 2 the direction of the needle 49 corresponds to the direction of the electromagnetic field indicated with arrow 29A, because the arrow 49 and the arrow 29A are parallel to each other. If the electromagnetic source 21 and the detector 25, 26 rotate while maintaining the position of the reconstructed volume, it is very likely that the direction of the needle 49 becomes congruent to the direction of some of the streamlines of the electric field 29, 29A, so that metal artefacts have to be expected. It should be noted that the electromagnetic field 20 may be an X-ray field, however, may be also any other electromagnetic field, if appropriate for the respective application.

In case, the electromagnetic field is an X-ray field, the source 21 may be an X-ray focal spot, however, any other source, in particular X-ray source may be used, if appropriate.

Figure 3:
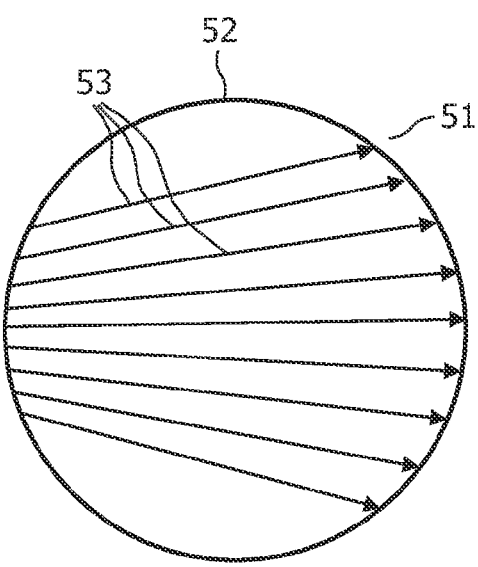
FIG. 3 illustrates a vector map over a reconstructed volume.

FIG. 3 illustrates a vector map 51 indicating a reconstructed volume 52 that shows the paths 53 of an X-ray cone beam 50 of FIG. 2 through the reconstruction, which are the needle directions that should be prevented. It should be noted that parallel vectors also means anti-parallel vectors, namely a vector direction plus/minus 180°.

FIG. 4 illustrates an examination exposure device 1 in form of a computer tomography. The examination exposure device comprises a device 10 for metal artefact prevention during metallic needle guidance within an electromagnetic field 20 of an examination exposure device. The exposure device may rotate on the longitudinal axis of the object to be examined, e.g. a human body. In case the needle position likely renders metal artefacts, the object to be examined may be shifted or rotated or moved such that no metal artefacts occur, wherein the original rotational axis of the examination apparatus is maintained, e.g. that of the longitudinal axis of the object to be examined 9 before being shifted to the alternative position 9A.

Figure 5:
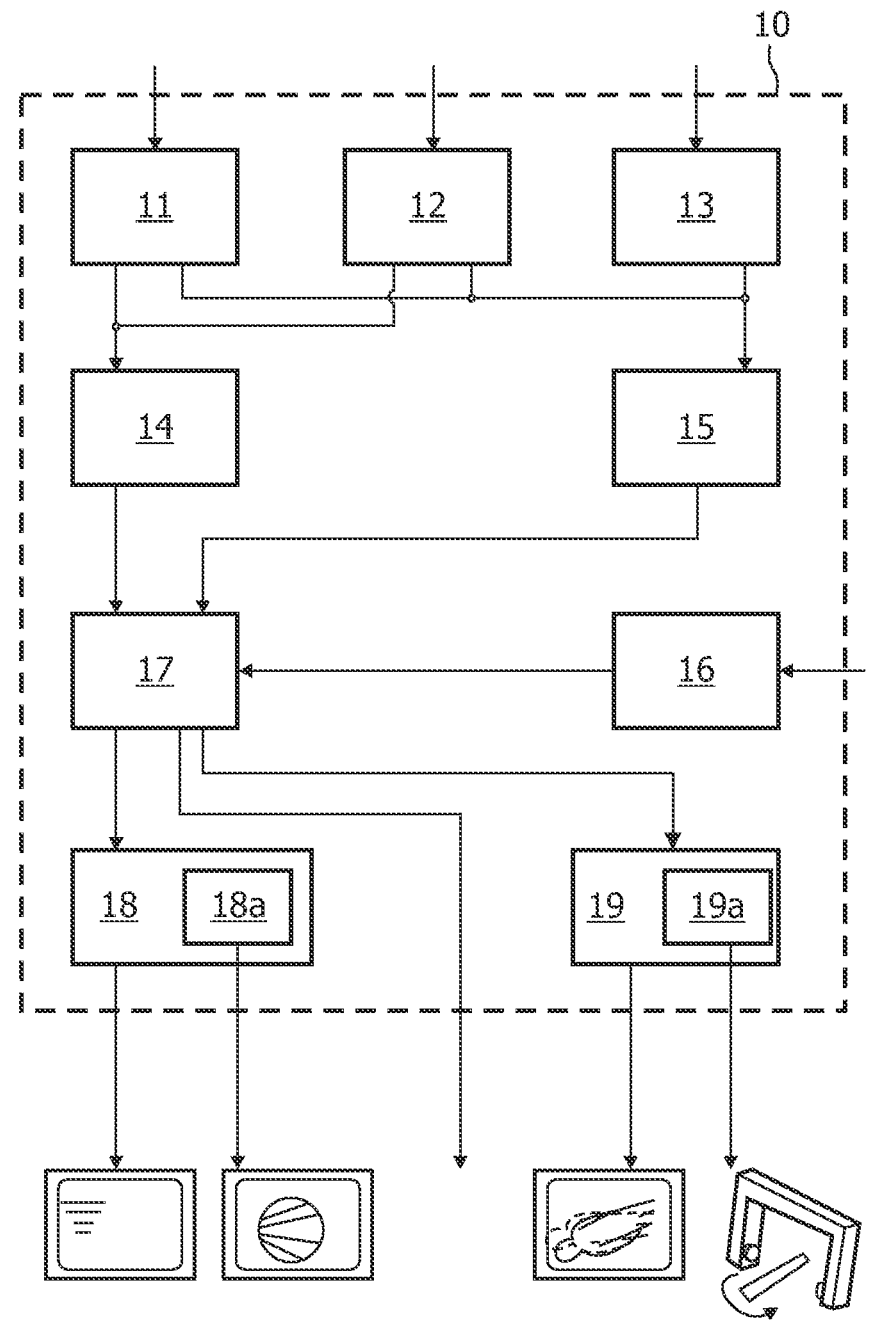
FIG. 5 illustrates a device according to one aspect of the present invention.

FIG. 5 illustrates the components and elements of the device 10. The device 10 comprises an element 11 adapted for determining a position of a source 21 of the electromagnetic fields 20. The arrow towards element 11 indicates the input of information needed for determining the position of a source. Further, there is provided an element 12 for determining a position of a detector 25, 26, wherein the arrow towards element 12 indicates the input of information to be inputted to determine the position of the detector. According to one aspect of the present invention, there is provided an element 13 for determining field influencing parameters in case that such field influencing parameters have to be considered.

Element 14 determines a direction 29 of the electromagnetic field 20 based on the position of the source 21 outputted by element 11 and the position of the detector 25, 26 outputted by element 12. According to one aspect of the present invention it is possible to additionally consider further field influencing parameters so that an element 15 may be provided for determining the direction of the electromagnetic field 20 based on the position of the source inputted by element 11, the position of the detector, inputted by element 12 and additionally the field influencing parameters inputted by element 13. It should be noted that element 13 and element 15 may be designed in a single unit, wherein element 13 may be included in element 15, or element 15 also takes over the tasks of element 13. Element 17 provides a signal based on a comparison of the determined direction 29 of the electromagnetic field 20 as provided by element 14 and of the direction 49 of the metallic needle 40 as provided by element 16. Element 16 determines the direction 49 of the metallic needle 40 and the arrow towards element 16 indicates input of information needed for determining the direction of the metallic needle. It should be noted that the electromagnetic field can be determined with or without considering field influencing parameters. The signal provided by element 17 may be used in different ways. A first possibility is just to output a signal by the device 10, as indicated by the middle output arrow of element 17. This signal may be used for further data processing. As an alternative, the signal may be provided to an element 18 for providing a warning to the user, for example as a warning text on a screen or any other appropriate warning. Alternatively, it is also possible to provide a vector map as described with respect to FIG. 3 by an element 18A, which is adapted for providing a vector map over a reconstructed volume that shows the paths of an X-ray cone beam through the reconstruction, which are the needle directions that should be prevented. The determination of the vector map may be carried out based on the information outputted by elements 11 to 17. The vector map can be displayed on a screen, on a printer or on any other appropriate medium.

As a further alternative, the device comprises an element 19 for providing an alternative position of the object to be examined 9 to be treated with a needle 40 such that the direction 49 of a needle 40 is not within paths 53 of an X-ray cone beam 50 through the reconstruction, which are the needle directions that should be prevented. The alternative position 9A of the object to be examined 9 may be indicated on a screen as a picture or as a text description or as any other appropriate indication. Any other indication medium is possible.

Further, it is possible to provide an element 19A for automatic positioning of the object to be examined such that the direction 49 of the needle 40 is not within paths 53 of an X-ray cone beam through the reconstruction which are the needle directions that should be prevented. As a matter of fact the automatic positioning may be carried out after receiving a confirmation of the user that the user agrees to an automatic positioning to avoid any danger in treating the object to be examined. The automatic positioning may influence for example the table where the object to be examined is placed. As a matter of fact it is also possible to move the examination apparatus where it is appropriate. Alternative position means that the position of the object to be examined and the examination device are moved with respect to each other.

It should be noted that the method as indicated in FIG. 1 may also be carried out as a programme element, which, when being executed by a processor, is adapted to carry out the method. The programme element may be also stored on a computer readable medium.

It should be noted that the term 'comprising' does not exclude other elements or steps, and the 'a' or 'an' does not exclude a plurality. Also elements described in association with different embodiments may be combined.

It should also be noted that reference signs and numbers in the claims shall not be construed as limiting the scope of the claims. The present invention may also be applied in the field of material science, non-destructive testing or other related applications.

The invention claimed is:

1. A visual artifact avoidance apparatus configured for visual-artifact prevention during guidance of an elongated instrument within an electro-magnetic field, said device comprising:
   an exposure device for examination of an object, said device comprising:
      a source of said field; and
      an image detector that includes a detector pixel, said device being configured for, via said source and said image detector, acquiring an image;
   a processor configured for:
      determining a position of said source, a position of said detector pixel, and a direction of a streamline of said electro-magnetic field between the two determined positions;
      determining, from the acquired image, a longitudinal direction of said elongated instrument;
      making a comparison between the two determined directions to check whether said two determined directions are parallel; and
      providing, in order to effect said prevention, a signal representative of an outcome of said comparison.

2. The apparatus of claim 1, said processor being further configured for providing, via at least one of a printer and a display, a vector map over a reconstructed volume that shows, through said volume, specifically a plurality of paths of respective constituent rays of an x-ray cone beam.

3. The apparatus of claim 2, the plural paths being such that, if a metallic needle, as said instrument, were to be aligned into coincidence with any of said plural paths during said guidance, such would give rise to visual artifacts.

4. The apparatus of claim 1, said detector comprising a plurality of detector pixels, said detector pixel being from among said plurality, said processor being configured for determining a plurality of directions of streamlines of said field for respective ones of the plural detector pixels, and, in order to effect said prevention, making a comparison between said direction of said instrument and respectively multiple ones of the plural directions.

5. The apparatus of claim 1, wherein said processor is further configured for, selectively based on said outcome, deciding whether to provide said signal.

6. The apparatus of claim 1, said detector comprising a plurality of detector pixels, said detector pixel being from among said detector pixels, said detector having a central location among said detector pixels, said detector pixel being offset from said central location.

7. The apparatus of claim 1, said instrument comprising, within said object, at least a portion having material that is radiopaque with respect to x-rays.

8. The apparatus of claim 7, said material being metallic.

9. The apparatus of claim 8, wherein said instrument comprises a needle.

10. The apparatus of claim 1, wherein said source is an x-ray focal spot.

11. The apparatus of claim 1, said field being provided by a radiation beam having an orientation, said processor being further configured for, in order to effect said prevention for said image, determining, for said orientation, a plurality of directions of streamlines of said field between corresponding pairs, each pair consisting of said source and a respective detector pixel.

12. The apparatus of claim 11, wherein at least part of said instrument, during said guidance, is within said object, and wherein said beam is an X-ray cone beam within said object.

13. The apparatus of claim 1, said processor being further configured for determining field influencing parameters, said direction of said streamline being based on additionally said field influencing parameters.

14. The apparatus of claim 1, said processor being further configured for providing a user warning that is based on the provided signal.

15. The apparatus of claim 1, said field being provided by an x-ray cone beam having an orientation, said processor being further configured for providing an alternative position of said object, said providing of said alternative position being such that the determined direction of said instrument is, for said alternative position, neither coincident with nor parallel to any from among a pre-selected plurality of spaced apart constituent ray paths of said beam in said orientation.

16. The apparatus of claim 15, wherein said constituent ray paths are paths of corresponding rays of said beam that are in a predetermined set of spaced apart directions.

17. The apparatus of claim 1, wherein said direction of said streamline of said field is a direction of a ray within a cone beam, said acquiring being performed via said cone beam.

18. The apparatus of claim 1, wherein said exposure device includes an imaging scanner.

19. The apparatus of claim 18, wherein said scanner is a computed tomography device.

20. The apparatus of claim 19, configured such that said beam is a wide X-ray cone beam.

21. The apparatus of claim 1, said electro-magnetic field being provided by a radiation beam having an orientation, said source emitting said beam.

22. The apparatus of claim 21, said detector having a plurality of detector pixels, said detector pixel being from among said detector pixels, said processor being configured for determining, for said orientation of said beam, directions of streamlines of said field between said position of said source and respectively positions of ones of the plural detector pixels, and for deciding whether said direction of said instrument is neither parallel to nor coincident with a direction from among said directions of streamlines.

23. The apparatus of claim 1, said apparatus being configured for said acquiring while said apparatus is in a given orientation, said processor being configured for said determining said direction of said streamline of said electro-magnetic field based on said apparatus being in said given orientation.

24. A non-transitory computer readable medium embodying a computer program for visual-artifact prevention during guidance of an elongated instrument within an electro-magnetic field, said program having instructions executable by a processor for performing a plurality of acts, from among said plurality there being the acts of:

determining a position of source of said electro-magnetic field, a position of a detector pixel, and a direction of a streamline of said electro-magnetic field between the two determined positions;

determining, from an image acquired by a detector that includes said pixel, a longitudinal direction of said elongated instrument;

making a comparison between the two determined directions to check whether said two determined directions are parallel; and providing, in order to effect said prevention, a signal representative of an outcome of said comparison.

* * * * *